United States Patent [19]

Levy

[11] Patent Number: 5,449,071

[45] Date of Patent: Sep. 12, 1995

[54] TRAY FOR MEDICAL SPECIMEN COLLECTION KIT

[76] Inventor: Abner Levy, 325 N. Oakhurst Dr., Beverly Hills, Calif. 90210

[21] Appl. No.: 145,070

[22] Filed: Oct. 28, 1993

[51] Int. Cl.⁶ .............................................. B65D 69/00
[52] U.S. Cl. .................................. 206/569; 206/570; 206/370; 206/564
[58] Field of Search ............... 206/569, 570, 571, 229, 206/370, 528, 564, 438

[56] References Cited

U.S. PATENT DOCUMENTS

| 3,935,944 | 2/1976 | Wilson et al. | 206/569 |
| 4,767,008 | 8/1988 | Wasnecke et al. | 206/370 X |
| 5,178,282 | 1/1993 | Williams | 206/570 |
| 5,181,394 | 1/1993 | Schea, III et al. | 206/570 X |

Primary Examiner—Jacob K. Ackun
Attorney, Agent, or Firm—Beehler & Pavitt

[57] ABSTRACT

A tray for packaging a medical specimen collection kit including a specimen vial containing a preservative fluid, an impermeable envelope containing a sterilizing fluid, and specimen collection implements. The tray has a first cavity for accomodating the vial horizontally, a second cavity sized for securely holding the vial in an upright position on the tray while the vial is uncapped during specimen collection, and a third cavity for containing the specimen collection implements. The first cavity may be formed in the bottom of a shallow recess for holding the envelope over the horizontally positioned vial.

22 Claims, 2 Drawing Sheets

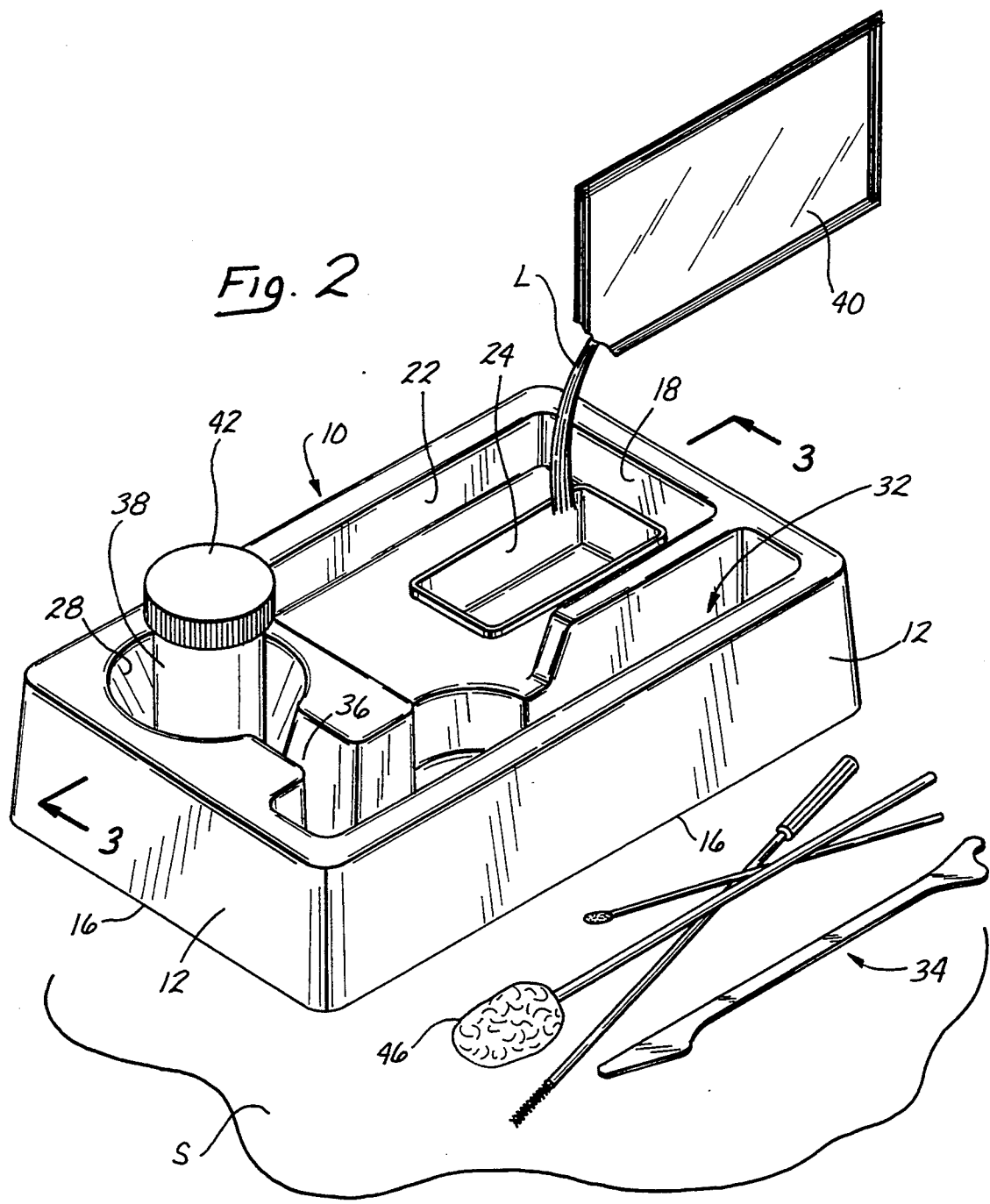

TRAY FOR MEDICAL SPECIMEN COLLECTION KIT

BACKGROUND OF THE INVENTION

1. Field of the Invention

This invention relates to implements employed for the collection and subsequent transportation to a diagnostic laboratory of biological specimens collected from a patient by medical personnel, and more specifically concerns a disposable tray compartmented for initially containing the specimen collection implements and subsequently serving as an aid during the specimen collection procedure.

2. State of the Prior Art

Numerous medical diagnostic procedures require the collection of a small sample of tissue or fluid from a patient for examination and analysis at a laboratory which may be distant from the specimen collection site. The specimen collection procedure may involve a preparatory step by which the area from which the specimen is to be collected is first cleansed, followed by the actual collection of the specimen from the body of the patient and placement of the medical specimen upon or into a suitable carrier which may be a glass slide or a container. A preservative may be applied to the specimen on the glass slide, or in the case of a vial, a quantity of preservative liquid is contained in the vial prior to placement thereinto of the specimen. Finally, the specimen carrier is itself placed in a package designed to protect both carrier and specimen during transport to the diagnostic laboratory location.

In order to facilitate the task of the medical personnel involved, many specimen collection kits have been developed which may include an assortment of collection implements, specimen carriers, a supply of antiseptic and specimen preservation liquids, as well as the protective packaging for delivery of the specimen to the laboratory. The contents of such kits varies depending on the specific type of medical specimen to be collected. Generally, however, such specimen collection kits have included disposable packages of chip board, which is a thin but relatively stiff type of cardboard, corrugated cardboard, or packages of vacuum formed thin plastic. Such kits have also been packaged on disposable trays, both simple trays as well as compartmented trays which are sealed in a plastic film covering for holding together the kit contents.

Very recently the FDA granted approval to a Pap Smear test procedure in which a tissue specimen is collected in the usual way from the patient's cervical area, but then placed in a small vial containing a preservative liquid. The vial containing the tissue specimen is then sent to the laboratory for analysis. This differs from prior Pap Smear collection procedures where the tissue specimen was deposited on a glass slide and treated with a fixative for preservation during transport to the diagnostic laboratory.

What is needed is a specimen collection kit which implements the newly approved procedure so as to speed and facilitate the procedure.

SUMMARY OF THE INVENTION

The present invention addresses this need by providing a disposable tray for containing and organizing articles and implements needed for collecting medical specimens for diagnostic purposes. The tray of this invention is particularly suited for a medical specimen collection kit which includes a specimen vial containing a preservative fluid for preserving the collected medical specimen for transport and delivery to the diagnostic site, and a separately packaged antiseptic liquid for swabbing the area of the area of the patient's anatomy from which the specimen is to be collected.

The tray of this invention has a first cavity dimensioned for containing the vial in a packaged condition, and a second cavity adapted to hold the vial in a specimen receiving position, in which the tray provides a wide, stable support base for the relatively small vial, to keep the vial from being accidentally tipped over during the specimen collection procedure. This significantly facilitates and expedites the collection of the specimen in that the medical personnel does not need to be concerned with possible spillage of the preservative liquid, and is not required to exercise great care when introducing the small specimen into the open vial. After the specimen is deposited into the vial, the tray support also facilitates and assists in capping the vial, particularly in single handed capping with a press fit plastic cap, again to prevent accidental spillage of the vial contents.

After removal of the vial from its initial packaged condition, the first cavity also serves as a receptacle for the antiseptic liquid provided with the kit. The antiseptic, such as acetic acid, may be contained in an impermeable envelope. Such a container although it is low cost, essentially unbreakable and compact and cannot be stood upright on a flat surface nor is it convenient for dipping a swab in its contents. The tray of this invention overcomes the shortcomings of such packaging in that the first cavity also serves as a basin for receiving the antiseptic liquid for convenient dipping of the swab by the medical technician during the specimen collection procedure. The tray preferably includes a pocket or recess for holding the container of antiseptic liquid. In the case of an impermeable envelope containing the antiseptic liquid, the pocket for the same may be integrated with the first cavity containing the specimen vial. In particular, the first cavity may have a lower portion dimensioned for holding the vial in a horizontal packaged condition and an upper portion configured to hold the impermeable envelope in overlying relationship with the specimen vial, such that both the vial and the envelope are contained below the tray top.

The second cavity for holding the vial in upright, specimen receiving position may have an upper generally funnel shaped surface for guiding insertion of the vial into a lower portion of the cavity which is dimensioned to make a retentive friction fit with the vial.

Preferably, a third cavity is provided in the tray for containing various manual implements used in the collection of the medical specimen. In a preferred form of the novel tray, the implement containing cavity communicates with the second cavity of the tray by means of a slot adapted to admit a finger of the hand used to remove the hand implements.

It is preferred to make the tray as a single unit of molded thermoplastic, such as a single thin sheet of vacuum formed thermoplastic.

A removable impermeable liner may be fitted in the first cavity of the tray for containing the antiseptic liquid, so that the liner, which after contact with the antiseptic liquid may require special disposal, may be disposed of separately to avoid special handling of the larger tray.

BRIEF DESCRIPTION OF THE DRAWINGS

FIG. 2 is a perspective view of the tray of FIG. 1, showing the specimen vial in specimen receiving position on the tray, the antiseptic liquid from the open envelope being poured into the removable liner in the vial packaging cavity, and an assortment of typical manual implements used in collection of medical specimen shown next to the tray.

DETAILED DESCRIPTION OF THE PREFERRED EMBODIMENTS

Figure 1:
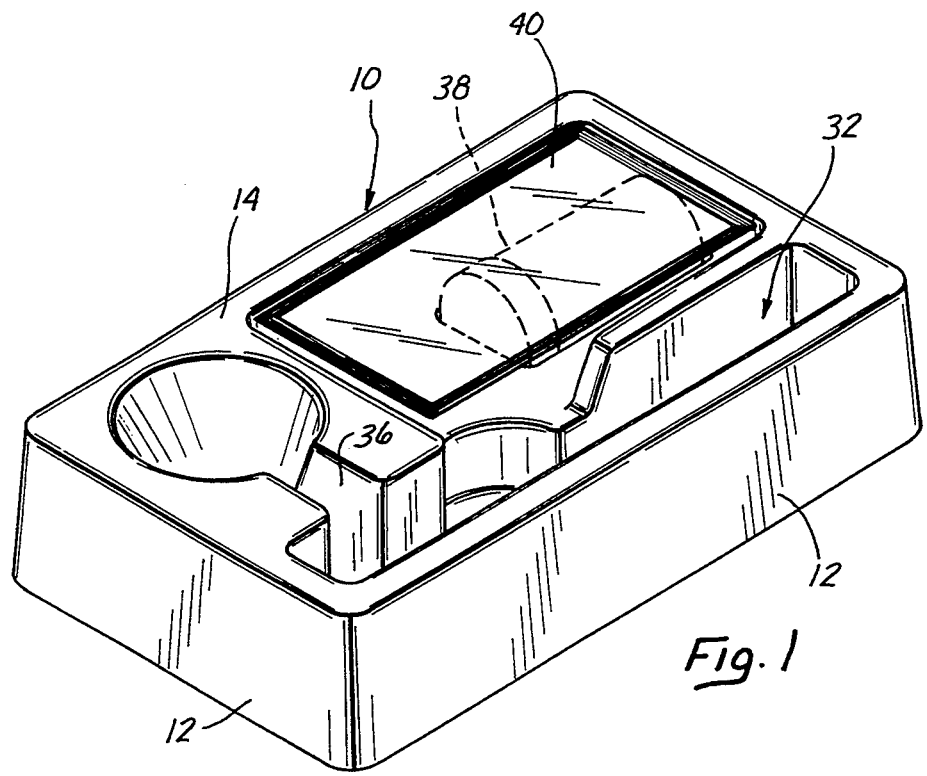
FIG. 1 is a perspective view of the specimen collection kit tray according to this invention, showing the specimen vial in packaged condition in phantom lining under the antiseptic liquid envelope.
Figure 3:
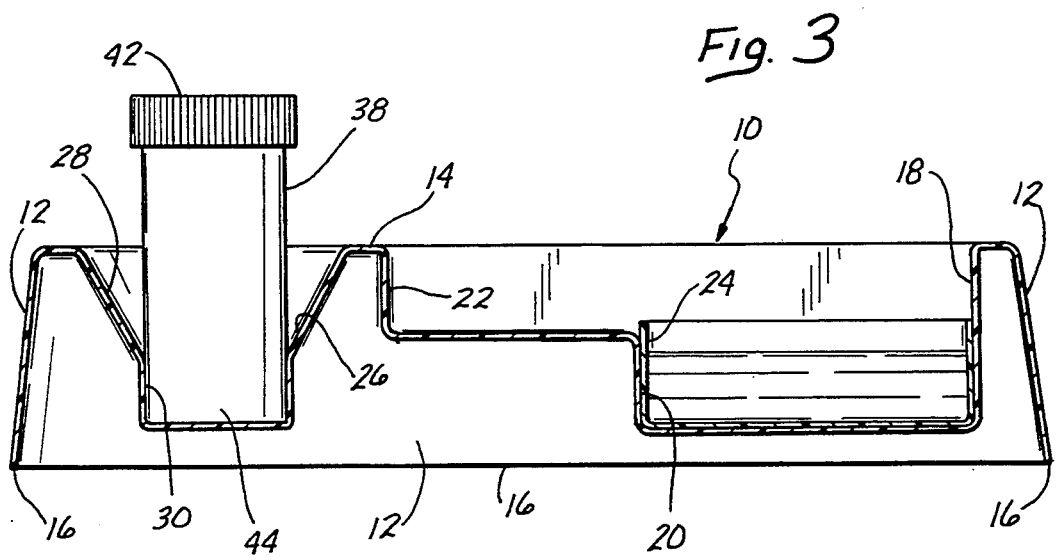
FIG. 3 is an elevational section of the tray taken along line 3—3 in FIG. 2.

With reference to the drawings, FIG. 1 shows a tray generally designated by numeral 10 for use in packaging a Pap Smear specimen collection kit. The tray 10 is molded of a single sheet of thermoplastic material and has four sides 12 which encompass and support a tray top 14. The lower edges 16 of the four sides 12 collectively define a base for the tray 10. As best appreciated by reference to FIG. 3, the tray 10 is made of a single relatively thin sheet of material formed to a three dimensional shape including a number of cavities defined by pockets suspended from tray top 14 and contained between the four side walls 12. A first tray cavity 18 has a rectangular lower recess 20 and a relatively shallow larger rectangular upper recess 22. A basin liner 24 in the form of a rectangular tub is placed in the lower recess 20 of the first cavity 18. The liner 24 can be easily separated and removed by hand from the tray 10. The liner 24 can be formed of thin thermoplastic sheet material similar to that of the tray 10. A second tray cavity 26 has a funnel shaped upper portion 28 axially aligned with a cylindrical lower portion 30. A third tray cavity 32 is of elongated shape and sized to contain various specimen collecting implements which are collectively designated by the numeral 34 in FIG. 2. The lower cavity portions 20, 30 and the third cavity 32 may all be of equal depth relative to the tray top 14. A finger slot 36 extends radially from the second cavity 28 and opens into the third cavity 32. The slot 36 has a depth similar to that of the second and third cavities 28, 32 respectively, and a width sufficient to readily accommodate an index finger moving from the second cavity 28 into the third cavity 32 for lifting the implements 34 lying in cavity 32.

A Pap Smear collection kit packaged according to this invention includes the tray 10, the specimen collection implements 34, a specimen vial 38 and an impermeable envelope 40. In the original packaged condition of the kit, the cylindrical vial 38 lies in the lower recess 20 of the first cavity 18 with its longitudinal axis horizontal, i.e., parallel to the tray top 14, as shown in phantom lining in FIG. 1. The width and length of the lower recess 20 may be slightly oversized with respect to the diameter and height, respectively, of the vial 38. The depth of the lower recess 20 may be about one half the diameter of the vial. The upper recess 22 is sized to closely receive the width and length of the impermeable envelope 40 when the envelope is laid flat over the vial 38, as seen in FIG. 1. The combined depth of the upper and lower recesses of the first tray cavity 18 is such as to contain both the vial 38 and envelope 40 just below the tray top 14. The implements 34 are placed in the third tray cavity 32. The tray is wrapped in a film, preferably transparent cellophane, which holds all the components of the kit in place, in their respective cavities of the tray 10.

In order to carry out the specimen collection procedure, the medical technician unwraps the tray 10, and places the tray on a stable supporting surface S as indicated in FIG. 2. The impermeable envelope 40 and the vial 38 are removed from the first tray cavity 18. The vial 38, which has a capped top end 42 and a closed bottom end 44, is inserted upright into the second tray cavity 26. Insertion of the lower end 44 of the vial is facilitated by the tapering, conical upper surface 28 of the tray cavity, which guides the lower end 44 into the close fitting lower portion 30 of the cavity. The lower portion 30 of the cavity is sized to make a relatively tight retentive friction fit with the vial, which is manually pressed into place therein by the medical personnel. The vial 38 is now in the specimen receiving position shown in FIGS. 2 and 3, and is secure against being accidentally tipped over during the specimen collection procedure. Pushing against the top of vial 38 in its specimen receiving position of FIGS. 2 and 3 only results in the tray 10 sliding along the supporting surface S, without risk of spillage of the vial contents. The vial 38 may be safely uncapped in this position and is then ready to receive the medical specimen to be collected. The envelope 40 is then opened, as by tearing off one of its corners and its liquid L contents are poured into the removable basin liner 24 as shown in FIG. 2. The envelope 40 contains an antiseptic liquid L in FIG. 2, specifically acetic acid, which is applied over the area from which the medical specimen is to be collected in order to neutralize microorganisms present in that area. The antiseptic liquid L is applied by saturating a swab 46 in the liquid contained in the basin liner 24. The liner 24 is stably supported against spillage because the wide base and low height of the tray 10 which makes it very difficult to upset on the surface S. Even if the tray 10 is jolted, so that the liquid L overflows the liner 24, the spillage is still contained within the upper portion 22 of the tray cavity 18, and no liquid is spilled onto the underlying surface S.

The medical specimen is collected using one or more of the implements 34, and the specimen is then introduced into the vial 42 which contains a preservative liquid. Once the specimen is transferred into the preservative liquid from the implement 34, the implement is withdrawn from the vial, and the vial is capped and separated from the tray 10 for forwarding to the diagnostic laboratory. The tray 10, all implements 34, and the empty envelope 40 are all single use disposable items, and are discarded upon completion of the specimen collection procedure. Since the acetic acid in the basin liner 24 is a potentially hazardous substance, the liner 24 can be conveniently handled in an environmentally appropriate manner separately from the bulkier tray 10 by simply lifting the liner 24 out of the tray. The tray 10 can be discarded as ordinary, non-hazardous trash, while the small liner basin 24 may be included with hazardous waste material for special handling.

The tray 10 if made of relatively flexible plastic material is shock resistant and light weight for safe and easy transport, and can be manufactured in large quantities at very low cost.

From the foregoing it will be appreciated that a tray for packaging and containing articles constituting a medical specimen collection kit has been disclosed, which not only provides low cost and effective packaging but is of considerable utility in facilitating the rapid and effective completion of the specimen collection procedure.

While a preferred embodiment of the invention has been described for purposes of clarity and example, it must be understood that many changes, substitutions and modifications to the described embodiment will be apparent to those possessed of ordinary skill in the art without thereby departing from the scope and spirit of the present invention, which is defined by the following claims.

What is claimed is:

1. A tray for packaging a medical specimen collection kit comprising:

a specimen vial containing a preservative fluid, the vial having a length between a capped top and a closed bottom and a particular cross-section and width, a generally planar impermeable envelope containing a sterilizing fluid, and one or more specimen collection implements;

tray means having a tray top and a tray base, a first cavity in said tray including a shallow upper recess with an upper floor or bottom sized to receive said envelope, a smaller lower recess defined in said upper floor having a length and a width closely sized to the length and width of said vial so as to closely contain said vial in a packaged horizontal condition below said upper floor with said envelope placed on said upper floor within said upper recess, a second cavity in said tray means closely dimensioned to said cross section of the vial for receiving and securing said vial upright on said tray means so that said tray means serves as a stabilizing base for the vial while a specimen is deposited therein to reduce the likelihood of spillage of said preservative fluid, and a third cavity in said tray means dimensioned for containing said one or more specimen collection implements.

2. The tray of claim 1 wherein said lower recess includes a removable impermeable liner sized to contain said vial.

3. The tray of claim 1 wherein said tray means are unitary.

4. The tray of claim 1 wherein said tray means is a single unit of molded thermoplastic.

5. The tray of claim 1 wherein said tray means is a single sheet of vacuum formed thermoplastic.

6. The tray of claim 1 wherein said second cavity has a lower portion dimensioned to make a friction fit with a lower end of said vial and a wider upper portion for facilitating insertion of the vial into said lower portion.

7. The tray of claim 1 wherein said vial has a longitudinal axis between a closed bottom and a capped top, said lower recess dimensioned for holding the vial horizontally relative to said tray top; said second cavity dimensioned for making a retentive fit with a lower portion of said vial in upright position.

8. The tray of claim 6 wherein said upper portion of said second cavity includes a generally funnel shaped surface for guiding insertion of the vial into said lower portion.

9. The tray of claim 1 wherein said upper recess is generally rectangular.

10. The tray of claim 1 further comprising a slot connecting said second and third cavities for admitting a finger of a hand seeking to remove said implements from said third cavity.

11. A medical specimen collection kit comprising:

a tray, a specimen vial having a closed bottom and a capped top and containing a first fluid, an impermeable envelope containing a second fluid, and one or more specimen collection implements;

said tray having a tray top, a tray base, and first, second and third cavities in said tray top, said first cavity including a lower recess dimensioned to closely contain said vial and an upper recess dimensioned to receive said envelope in overlying relationship with said vial, said second cavity dimensioned for making a retentive fit with said vial in upright position, said third cavity being dimensioned for containing said one or more specimen collection implements.

12. The tray of claim 11 wherein said lower recess includes a removable impermeable liner sized to contain said vial in said horizontal position.

13. The tray of claim 11 wherein said tray means is a single sheet of vacuum formed thermoplastic.

14. The tray of claim 11 wherein said second cavity includes a generally funnel shaped surface for guiding insertion of the vial thereinto.

15. A medical specimen collection kit including a cylindrical specimen vial containing a preservative fluid, a tray, and first and second cavities in said tray, said first cavity being generally rectangular and dimensioned for containing said vial horizontally in a packaged position, said second cavity being generally circular and dimensioned for closely receiving a bottom end of said vial thereby to support said vial in specimen receiving upright position on said tray, such that the tray serves as a stable base for said vial to prevent spillage of the preservative fluid during deposition of a specimen thereinto.

16. The tray of claim 15 wherein said second cavity is dimensioned to make a friction fit with said vial.

17. The tray of claim 15 wherein said second cavity includes a sloping upper surface of enlarged aperture relative to a diameter of said cylindrical vial for guiding insertion of said bottom end thereinto.

18. The tray of claim 15 further comprising a removable impermeable liner in said first cavity sized to contain said vial.

19. The tray of claim 15 further comprising a third cavity in said tray for containing specimen collection implements.

20. A medical specimen collection kit comprising:

a unitary tray formed of molded thermoplastic, a specimen vial having a closed bottom and a capped top and containing a first fluid, an impermeable envelope containing a second fluid, and one or more specimen collection implements;

said tray having a tray top, a tray base, and first, second and third cavities in said tray top, said first cavity a lower recess dimensioned to closely contain said vial and an upper recess dimensioned to receive said envelope in overlying relationship with said vial, said second cavity being generally cylindrical for making a retentive friction fit with said vial in upright position on said tray, said third cavity dimensioned for containing said one or more specimen collection implements.

21. A medical specimen collection kit comprising:

a tray having a tray top, a base, and first and second cavities in said tray top, a specimen vial having a bottom and a capped top, a removable impermeable liner in said first cavity, said liner being dimensioned for containing said vial in a packaged horizontal position below said tray top, said second cavity being dimensioned to make a friction fit for supporting said vial in specimen receiving upright position on said tray.

22. A medical specimen collection kit including a specimen vial containing a preservative fluid, the vial having a length between a capped top and a closed bottom and a particular cross-section and width, a tray, first and second cavities in said tray, said first cavity being dimensioned for holding said vial horizontally on said tray, said second cavity conforming to said cross section and dimensioned for making a friction fit with a bottom end of said vial thereby to support said vial in specimen receiving upright position on said tray, such that the tray serves as a stable base for said vial to prevent spillage of the preservative fluid during deposition of a specimen thereinto.

* * * * *